United States Patent
Klemm

[11] Patent Number: 5,843,039
[45] Date of Patent: Dec. 1, 1998

[54] SURGICAL TREATMENT

[75] Inventor: Bernd Klemm, Recklinghausen, Germany

[73] Assignee: Karl Storz GmbH & Co., Tuttlingen, Germany

[21] Appl. No.: 809,259

[22] PCT Filed: Sep. 8, 1995

[86] PCT No.: PCT/EP95/03525

§ 371 Date: Mar. 13, 1997

§ 102(e) Date: Mar. 13, 1997

[87] PCT Pub. No.: WO96/08204

PCT Pub. Date: Mar. 21, 1996

[30] Foreign Application Priority Data

Sep. 14, 1994 [DE] Germany .......................... 44 32 673.4

[51] Int. Cl.⁶ .................................................. A61M 5/178
[52] U.S. Cl. .......................................... 604/164; 606/185
[58] Field of Search ............................ 606/185; 604/164, 604/158, 161, 168

[56] References Cited

U.S. PATENT DOCUMENTS 5,224,951  7/1993  Freitas .
5,256,147  10/1993 Vidal et al. .
5,352,206  10/1994 Cushieri et al. ......................... 606/185

FOREIGN PATENT DOCUMENTS 0 604 197 A2  6/1994  European Pat. Off. .
WO 93/10837  6/1993  WIPO .
WO 93/17626  9/1993  WIPO .

Primary Examiner—Michael Buiz
Assistant Examiner—Kevin Truong

[57] ABSTRACT

The invention concerns a surgical instrument whose distal end region is to be introduced or inserted by a puncture into a cavity of a patient's body. The surgical instrument has an outer trocar sleeve (1) and a trocar mandrel (2) which can be inserted in the latter and is guided in a sliding manner. When slid into an end position, the distal tip (4) of the trocar mandrel (4) projects beyond the end region (3) of the trocar sleeve (1), which end region is inclined relative to the longitudinal axis of the sleeve. In order to keep the distance between the trocar mandrel tip (4) and the distal end (6) of the trocar sleeve (1) as small as possible and to reduce the risk of injury to the patient when the surgical instrument is inserted by a puncture, it is proposed according to the invention that the trocar mandrel tip (4) is eccentric relative to the longitudinal axis of the trocar mandrel and is disposed in the region of the distal end (6) of the trocar sleeve (1) facing the patient.

15 Claims, 2 Drawing Sheets

SURGICAL TREATMENT

BACKGROUND OF THE INVENTION

The invention concerns a surgical instrument whose distal end region is to be introduced or inserted by a puncture into a cavity of a patient's body, the surgical instrument having an outer trocar sleeve and a trocar mandrel which can be inserted in the latter and is guided in a sliding manner, whereby, when slid into an end position, the distal tip of the trocar mandrel projects beyond the end region of the trocar sleeve, which end region is inclined relative to the longitudinal axis of the sleeve.

Surgical instruments of the type mentioned at the outset are used in minimum invasive surgery for diagnosis and surgery on the living body of a patient.

Thus to perform an intraabdominal operation, first an insufflation needle is passed through the patient's abdominal cavity. This hollow insufflation needle is connected by tubing to a gas source to enable the patient's abdominal cavity to be filled with gas and suitably dilated. After the abdominal cavity has been dilated, the surgical instrument is inserted by a puncture, practically blindly, into the body cavity, the trocar mandrel being inserted in the trocar sleeve and the trocar mandrel tip projecting beyond the distal end of the sleeve.

After the surgical instrument has been inserted by a puncture, the trocar mandrel can be removed from the trocar sleeve and replaced by optical observing instruments, grippers, thread holders, forceps or similar surgical instruments.

The trocar mandrel is usually cone-shaped at its trocar mandrel tip, so as to facilitate piercing through the layers of tissue. Trocar mandrels with polygonal trocar mandrel tips have also already been provided, these acting like a knife and practically opening the intractable peritoneum. However these usually three-edged trocar mandrel tips have the drawback of producing severe and large lacerations in the event of inadvertent injury.

To facilitate pushing the trocar sleeve further after the peritoneum has been pierced with the aid of the trocar mandrel, it is already known that the distal end of the trocar sleeve be arranged slantwise relative to the longitudinal axis of the sleeve. For the slanted sleeve opening of the trocar sleeve meets with less resistance by tissue, so that the trocar sleeve can slide better.

The so-called "tent" phenomenon during insertion of the trocar mandrel by a puncture is known, according to which the intractable peritoneum recedes inwardly to the pointed trocar mandrel and deflects in a "tent-like" fashion before the puncture wanted is established. In so doing, the trocar mandrel tip is liable to enter the vicinity of the abdominal organs, substantially increasing the risk of considerable injury to the patient.

Excessive penetration of the trocar mandrel inserted in the trocar sleeve into a cavity of the body can lead to mortal injuries to internal organs or blood vessels by the trocar mandrel tip.

A surgical instrument having a piercing means insertable in a trocar is already known from U.S. Pat. No. 5,224,951. This piercing means has an outer cutting sleeve in which a protective rod is guided in a sliding manner. The distal end of the outer cutting sleeve is disposed inclined relative to the longitudinal axis of the sleeve in such a way that the distal end edge of the sleeve tapers to a two-bladed puncturing tip situated to the fore as considered in the direction of puncture. As soon as the piercing means of the known surgical instrument meets the body tissue, the protective rod can move slightly into the interior of the sleeve so that the puncturing tip is cleared. The protective rod, which in practice is formed as a blunt plastic part, has at its distal end two slanted flanks which are to prevent the tissue from being cored by the keen edge of the outer cutting sleeve, as well to prevent cored pieces of tissue from entering the interior of the sleeve.

Since in the known surgical instrument according to U.S. Pat. No. 5,224,951 the cutting sleeve tapers slantwise at its distal end to a puncturing tip and is provided for a trocar whose distal end is disposed at right angles to the longitudinal axis of the trocar, here as well the distal end of the cutting sleeve has to be advanced outwards a long way beyond the adjacent end of the trocar. The risk of injury, which is anyway already high because of the two-bladed puncturing tip, is therefore further increased.

In WO-A-93/17626 a surgical instrument is described in which the trocar mandrel guided in a sliding manner in a trocar sleeve co-operates with a retracting device disposed at the proximal end of the trocar sleeve. The retracting device holds the trocar mandrel in its advanced operative position as the tissue is pierced and retracts it into the trocar sleeve as soon as the trocar mandrel is relieved. However, to assume its piercing position the trocar mandrel tip, which in some embodiments of WO-A-93/17626 is also eccentric relative to the longitudinal axis of the trocar mandrel, has to be advanced a long way beyond the distal end of the trocar sleeve disposed at right angles to the longitudinal axis of the sleeve. This again produces an unnecessarily long sliding path and a correspondingly high risk of injury as the trocar mandrel is inserted by a puncture and as the trocar sleeve is pushed further.

A surgical instrument is already known from U.S. Pat. No. 5,256,147 in which a plurality of replaceable trocar mandrel tips are associated with the trocar mandrel that is guided in a sliding manner in a trocar sleeve. The trocar mandrel of the known surgical instrument has for this purpose a trocar mandrel shank on which one trocar mandrel tip at a time can be fixed in a detachable fashion. In the use position inserted in the trocar sleeve, this trocar mandrel tip is securely retained on the trocar mandrel shank and partially projects beyond the trocar sleeve end oriented at right angles to the longitudinal axis of the sleeve. The known surgical instrument according to U.S. Pat. No. 5,256,147 has, inter alia, trocar mandrel tips with slanted tip ends. However, these trocar mandrel tips also have to be advanced a long way beyond the end opening of the trocar sleeve, this entailing the risks mentioned for the patient.

A surgical instrument with a trocar sleeve is already described in EP 0 604 197 A2, in which the distal sleeve opening facing the patient is occluded by means of a safety shield. This safety shield is composed of a plurality of generally conically disposed parts which, as a trocar mandrel is advanced, spring outwards and clear the sleeve opening between them. Here, too, the trocar mandrel has to be advanced further beyond the sleeve opening to assume its puncturing position, in order that its trocar mandrel tip also projects beyond the lateral parts of the safety shield.

A surgical instrument constituting a combination of an outer trocar sleeve and, slidably guided in the latter, an inner needle or cannula, is already known from WO-A-93/10837. While the trocar sleeve here also has a sleeve opening oriented at right angles to the longitudinal axis of the sleeve, the needle or cannular has a distal end disposed at an inclination to its longitudinal axis. To reduce the risk of injury involved by the needle tip projecting a long way beyond the opening of the trocar sleeve, it is proposed in WO-A-93/10837 that, upon pressure relief, the needle or cannula is automatically retracted into the interior of the trocar sleeve. However, by this means the needle tip projecting a long way beyond the trocar sleeve cannot be prevented from leading to inadvertent injury until such time as it is situated inside the sleeve.

SUMMARY OF THE INVENTION

The object underlying the invention is therefore particularly to provide a surgical instrument of the type mentioned at the outside, whose use involves a substantially smaller risk of injury to the patient.

This object is accomplished according to the invention in the surgical instrument of the kind mentioned at the outset particularly in that the trocar mandrel tip is eccentric relative to the longitudinal axis of the trocar mandrel and is disposed in the region of the distal end of the trocar sleeve facing the patient.

The eccentric arrangement of the trocar mandrel tip permits the distance between the distal tip of the trocar mandrel and the respective end of the trocar sleeve to be kept comparatively small. By virtue of the eccentric arrangement of the trocar mandrel tip, the sliding path necessary as the trocar mandrel is inserted by a puncture and as the trocar sleeve is pushed further is considerably reduced. As a smaller sliding path is necessary for piercing, for instance, the patient's abdominal wall (of the peritoneum) with the aid of the surgical instrument according to the invention, the risk of inadvertent injury to the patient's internal organs and blood vessels is also reduced.

In order that as it pierces, the trocar mandrel tip meets with as little resistance as possible by the tissue, a preferred embodiment of the invention proposes that the distal end region of the trocar mandrel essentially takes the form of an intersection or a curve of intersection between a cylinder oriented approximately in the longitudinal direction of the sleeve and a cone. The end surface facing the patient of the trocar mandrel according to the invention is therefore also essentially adapted to a part of the surface of a cone.

In performing known operation methods in which, after having dilated the abdominal cavity, the surgical instrument comprising trocar sleeve and trocar mandrel is pierced, practically blindly, through the patient's layers of tissue, it is suitable if the cone tip of the trocar mandrel adapted to part of the surface of a cone is disposed outside the cross section of the trocar or approximately on the circumference of the trocar mandrel. Particularly if the trocar mandrel tip is arranged approximately on the circumference of the trocar mandrel, this trocar mandrel tip, here also tapering to a point, projects only slightly beyond the distal end of the trocar sleeve.

An advantageous further development according to the invention proposes that the trocar tip is disposed within the cross section of the trocar mandrel and is preferably spaced from the longitudinal axis of the trocar mandrel on the one hand and from the circumference of the trocar mandrel on the other. Such a trocar mandrel tip offset relative to the longitudinal axis of the trocar mandrel as well as relative to the circumference of trocar mandrel permits the configuration of a comparatively flat plane of the tip which can be of advantage particularly for smaller trocars.

The trocar mandrel tip of the surgical instrument according to the invention can taper to a point. It is also possible, however, that the trocar mandrel tip is of knife-shaped configuration or is slightly rounded off at the end. Particularly with a trocar mandrel tip slightly rounded off at the end, the risk of injury can be reduced even further.

A preferred embodiment of the invention proposes that the trocar mandrel and/or the trocar sleeve is/are provided with at least one anti-rotation means which is operative at least in an end position of slide and serves to safeguard the relative position of trocar sleeve and trocar mandrel in their circumferential direction. In this embodiment, the rotary position or relative position between trocar sleeve and trocar mandrel is safeguarded in the end position of slide in which the eccentric trocar mandrel tip is disposed in the region of the distal end of the trocar sleeve facing the patient. It may be advantageous in this regard if these anti-rotation means are lockable so that the two instrument parts do not have to be held in their end position of slide by the operating surgeon.

It is suitable if provided at the proximal end region of the trocar mandrel or trocar sleeve is at least one anti-rotation projection which, at least in an end position of slide, engages with an anti-rotation recess of the other instrument part. For instance, this anti-rotation projection can be provided at the proximal end region forming a handle of the trocar mandrel, in an end position of slide this anti-rotation projection engaging with an anti-rotation recess provided at the adjacent proximal end of the trocar sleeve.

The trocar mandrel of the surgical instrument according to the invention preferably has a trocar mandrel tip substantially adapted in shape to a part of the surface of a cone. The trocar mandrel can also have a surface tapering with a convexity or concavity to its trocar mandrel tip.

Another embodiment and further development of the invention concerns a surgical instrument of the type mentioned at the outset in which at least one gas duct terminating in the region of a gas inlet opening or gas outlet opening of the trocar sleeve is provided between the trocar mandrel and the trocar sleeve. With the aid of such a gas duct between the trocar mandrel and the trocar sleeve, the escape of gas at the gas outlet opening of the trocar sleeve permits that during the conventional process of insertion one can determine when the surgical instrument has pierced the patient's peritoneum dilated by means of the insufflation needle. In such a surgical instrument it is proposed according to the invention that a signalling whistle is downstream of the gas outlet opening of the trocar sleeve, as considered in the direction of outflow. With the aid of such a signalling whistle it can be determined with a substantially greater degree of reliability whether the surgical instrument has penetrated the peritoneum and whether the gas previously introduced into the abdominal cavity is escaping by way of the gas outlet opening of the trocar sleeve. Since further advancement of the surgical instrument into the abdominal cavity can be stopped or at least slowed down when the signalling whistle sounds, inadvertent injury to the patient is also avoided.

It is advantageous in this regard if the trocar mandrel has between its two end regions a portion of reduced cross section defining a gas duct between the trocar mandrel and the inside wall of the trocar sleeve, and if provided at the distal end region of the trocar mandrel is a preferably groove-like duct portion leading from the trocar mandrel tip to the reduced cross-sectional region of the trocar mandrel. This trocar mandrel formed with a reduced cross section in a comparatively large portion of its longitudinal expanse can be cleaned particularly well.

The portion of reduced cross-section of the trocar mandrel can have by way of example a cross-shaped section or be composed only of three or four connecting rods joining the front part - possibly solid in design - of the trocar mandrel to the proximal end region taking the form of a handle of the trocar mandrel.

Further features of the invention follow from the following description of exemplary embodiments of the invention, taken in conjunction with the claims and the drawings. The individual features may be realized singly or severally in an embodiment of the invention.

DETAILED DESCRIPTION OF THE DRAWINGS

Figure 1:
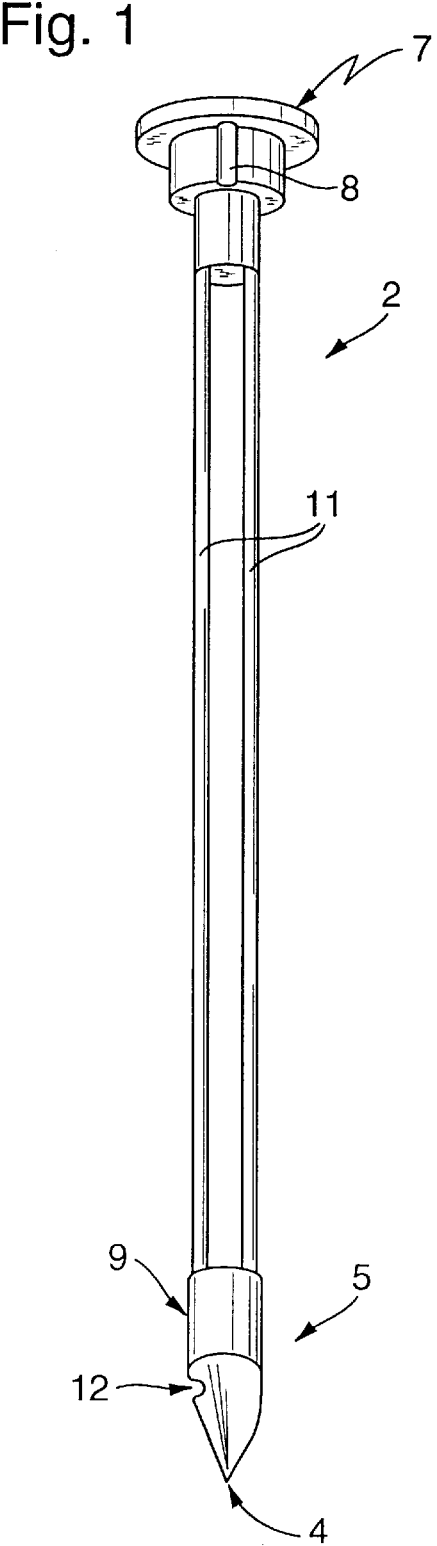
FIG. 1 is a perspective view of a trocar mandrel having a trocar mandrel tip that is eccentric relative to the longitudinal axis of the trocar mandrel.
Figure 2:
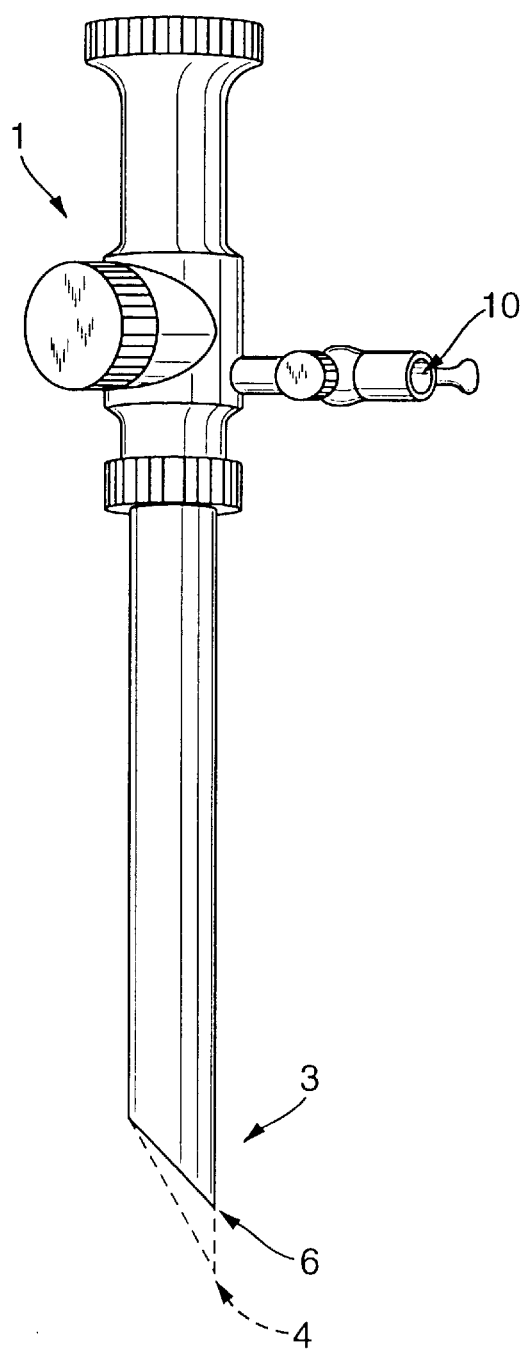
FIG. 2 is a perspective view of a trocar sleeve associated with the trocar mandrel of FIG. 1, this trocar sleeve and the trocar mandrel composing a surgical instrument.

FIG. 2 depicts a trocar sleeve 1 in which a trocar mandrel 2, shown in FIG. 1, is guided in a sliding manner. Trocar sleeve 1 and trocar mandrel 2 compose a surgical instrument which is usable in minimum invasive surgery and for that purpose can be inserted by a puncture into the cavity of a patient's body.

For inserting the surgical instrument by a puncture, the trocar mandrel 2, when inserted in the trocar sleeve 1 and slid into an end position, projects beyond the distal end region 3 of the trocar sleeve 1. At the same time, the sleeve opening provided at the distal end region 3 of the trocar sleeve 1 is slanted relative to the longitudinal axis of the trocar sleeve so as to facilitate pushing the trocar sleeve 1 further as the surgical instrument is inserted.

The trocar mandrel tip 4 of the trocar mandrel 2 is arranged eccentrically relative to the longitudinal axis of the trocar mandrel. As becomes apparent from FIG. 1, the distal end region 5 of the trocar mandrel 2 is essentially formed as an intersection or a curve of intersection between a cylinder oriented approximately in the longitudinal direction of the sleeve and a cone. The cone tip of this cone, which here simultaneously also composes the trocar mandrel tip 4, is arranged on the circumference of the trocar mandrel and tapers to a point.

By means of the eccentric configuration of the trocar mandrel tip 4 and its arrangement in the region of the foremost end 6 of the trocar sleeve 1 facing the patient, the trocar mandrel tip 4 indicated by dashed lines in FIG. 2 nevertheless projects only slightly beyond the distal opening of the trocar sleeve 1. The distance between the foremost end 6 of the trocar sleeve 1 and the adjacent trocar mandrel tip 4 is thereby substantially reduced and the surgical instrument has to be advanced less far through the abdominal wall until the trocar sleeve has penetrated the by nature intractable peritoneum receding in a "tent-like" fashion.

Provided at the proximal end region taking the form of a handle 7 of the trocar mandrel 2 is an anti-rotation projection 8 which, in the end position of slide, engages with a corresponding anti-rotation recess (not shown) provided at the adjacent proximal end of the trocar sleeve 1.

As becomes apparent from FIG. 1, the distal front part 9 of the trocar mandrel is a solid element and has a substantially cylindrical outer circumference corresponding to the inside diameter of the trocar sleeve 1. In the portion arranged between the handle 7 of the trocar mandrel 2 and the tip 4 or front part 9 of the trocar mandrel, the trocar mandrel 2 has a reduced cross section defining a gas duct between the trocar mandrel and the inside wall of the trocar sleeve. When the trocar mandrel is slid into the end position, the gas duct terminates in a gas inlet and outlet opening 10 of the trocar sleeve 1.

In this reduced cross-sectional region of the trocar mandrel 2 there are only four connecting rods 11 joining the handle 7 of the trocar mandrel to the front part 9 of the trocar mandrel. Of these four connecting rods 11, only two rods 11 are to be seen in FIG. 1.

Provided at the distal end region 5 of the trocar mandrel 2 is a groove-like duct portion 12 leading from the trocar mandrel tip 4 to the reduced cross-sectional region of the trocar mandrel 2.

Once the surgical instrument has been inserted by a puncture and the front part 9 of the trocar mandrel has in a known manner penetrated the peritoneum of the abdominal cavity dilated by gas insufflation, this is indicated to the operating surgeon when the gas fizzes from there, escaping by way of the duct portion 12, by way of the gas duct kept free by the connecting rods 11 and by way the gas outlet opening 10 of the trocar sleeve 1.

It may be suitable in this connection if a signalling whistle is downstream of the gas outlet opening 10 of the trocar sleeve 1, as considered in the direction of outflow. When the signalling whistle sounds, the operating surgeon can slow down or stop the process of insertion by a puncture before he inadvertently injures the patient's internal organs or vessels.

Figure 3:
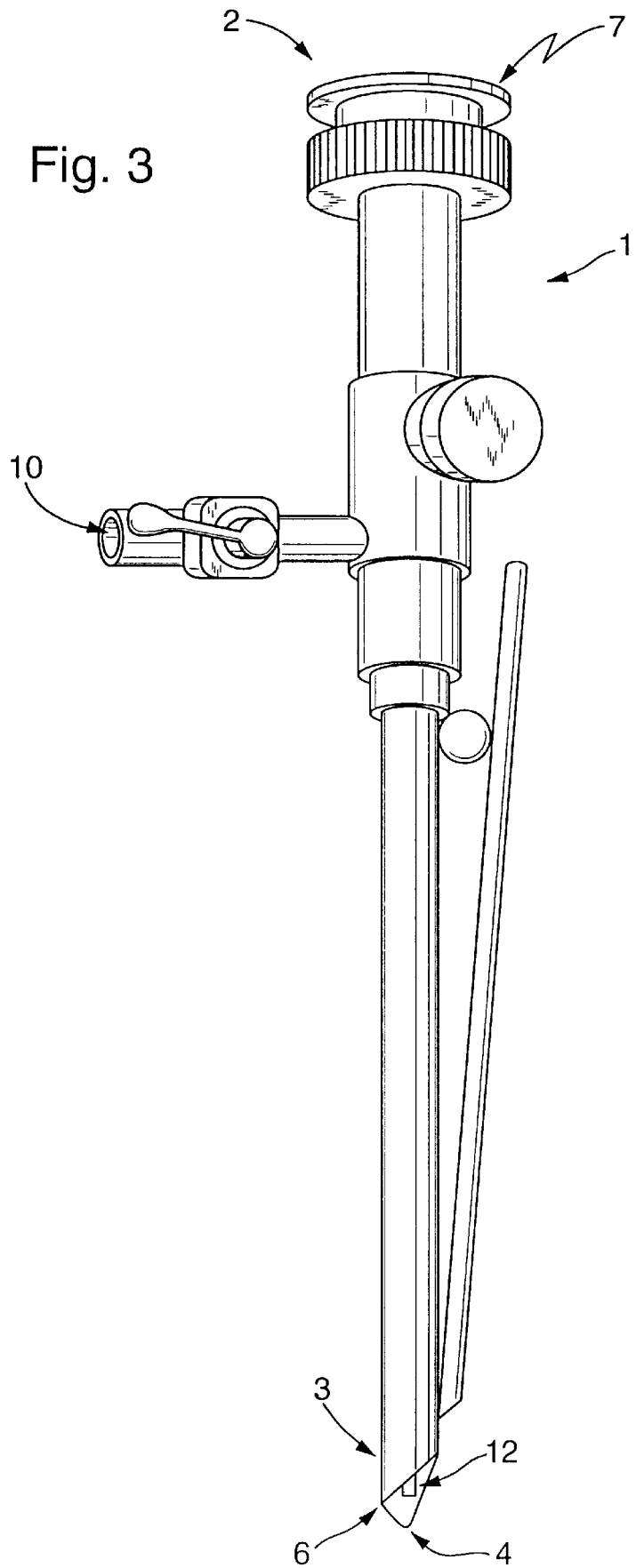
FIG. 3 is a surgical instrument, similar to that of FIGS. 1 and 2, with the trocar mandrel of this surgical instrument inserted in the trocar sleeve.

FIG. 3 shows a surgical instrument whose trocar mandrel tip 4 is likewise eccentric relative to the longitudinal axis of the trocar mandrel and is adapted to part of the surface of a cone. The trocar mandrel tip 4 is provided within the cross section of the trocar mandrel and is spaced from the longitudinal axis of the trocar mandrel on the one hand, and from the circumference of the trocar mandrel on the other. This arrangement of the trocar mandrel tip 4, as depicted in FIG. 2, permits a flatter plane of the tip to be provided, particularly for trocar sleeves of smaller diameter.

As FIG. 3 shows, the trocar mandrel tip 4 is slightly rounded off here, so as to additionally reduce the risk of injury by the surgical instrument depicted in FIG. 3.

To sum up it can be said that, by virtue of the eccentric configuration of the trocar mandrel tip 4 relative to the longitudinal axis of the trocar mandrel and by virtue of disposing this trocar mandrel tip 4 at the distal end of the trocar sleeve 1 facing the patient, the risk of injury to the patient when the surgical instrument is inserted by a puncture is substantially reduced.

I claim:

1. A surgical instrument having a distal end region adapted for introduction into a body cavity by a puncture, comprising:

an outer trocar sleeve (1) having a longitudinal axis, an end region (3), a sleeve distal end (6) and a proximal end; and a trocar mandrel (2) having a longitudinal axis, a cross section, a mandrel distal end region (5), a distal tip (4), and a mandrel proximal end; wherein said trocar mandrel (2) is insertable into said outer trocar sleeve (1) such that said mandrel distal end region (5) of said trocar mandrel (2) is disposed within said end region (3) of said outer trocar sleeve (1) and said distal tip (4) is offset from the central longitudinal axis of said trocar mandrel (2).

2. The surgical instrument according to claim 1, wherein said mandrel distal end region (5) is formed as an intersection between a cylinder oriented approximately in a direction of the longitudinal axis and a cone.

3. The surgical instrument according to claim 1, wherein said distal tip (4) projects beyond said end region (3) of said outer trocar sleeve (1), and said sleeve distal end (6) is inclined relative to the longitudinal axis of said sleeve (1).

4. The surgical instrument according to claim 1, wherein said distal tip (4) is displaced inwardly from a circumference of said trocar mandrel (2).

5. The surgical instrument according to claim 1, wherein said distal tip (4) is displaced one of outside of said cross section of said trocar mandrel (2) and on a circumference of the trocar mandrel (2).

6. The surgical instrument according to claim 1, wherein said distal tip (4) has a knife-shaped configuration.

7. The surgical instrument according to claim 1, wherein said distal tip (4) has a cone-shaped configuration.

8. The surgical instrument according to claim 1, wherein said distal tip (4) is slightly rounded at the end.

9. The surgical instrument according to claim 1, further comprising at least one anti-rotation means located on at least one of the trocar mandrel (2) and the trocar sleeve (1), the anti-rotation means being operative at least in an end position of insertion to prevent rotation of said trocar mandrel (2) relative to said outer trocar sleeve (1).

10. The surgical instrument according to claim 1, further comprising an anti-rotation projection (8) provided on said proximal end of said trocar mandrel (2) and an anti-rotation recess provided on said proximal end of said trocar sleeve (1), wherein said anti-rotation projection (8) is adapted for engagement with said anti-rotation recess to prevent rotation of said trocar mandrel (2) in said outer trocar sleeve (1).

11. The surgical instrument according to claim 1, wherein said trocar mandrel (2) has a surface which tapers relative to said distal tip (4).

12. The surgical instrument according to claim 11, wherein said tapering is convex relative to said distal tip (4).

13. The surgical instrument according to claim 11, wherein said tapering is concave relative to said distal tip (4).

14. The surgical instrument according to claim 1, further comprising at least one gas duct provided between said trocar mandrel (2) and said trocar sleeve (1), a gas opening (10) provided on said trocar sleeve (1) and a signaling whistle, wherein said gas duct terminates at said gas opening (10) and said signaling whistle is downstream of said gas opening.

15. The surgical instrument according to claim 1, further comprising a gas duct located between said trocar mandrel (2) and the inside wall of said trocar sleeve (1), said gas duct being defined by a portion of reduced cross section of said trocar mandrel (2) between the proximal end and said distal end region (3) of said trocar mandrel (2), wherein said distal tip (4) further comprises a groove-like duct portion (12) leading from said distal tip (4) to said reduced cross section of said trocar mandrel (2).

* * * * *